Figure 1:
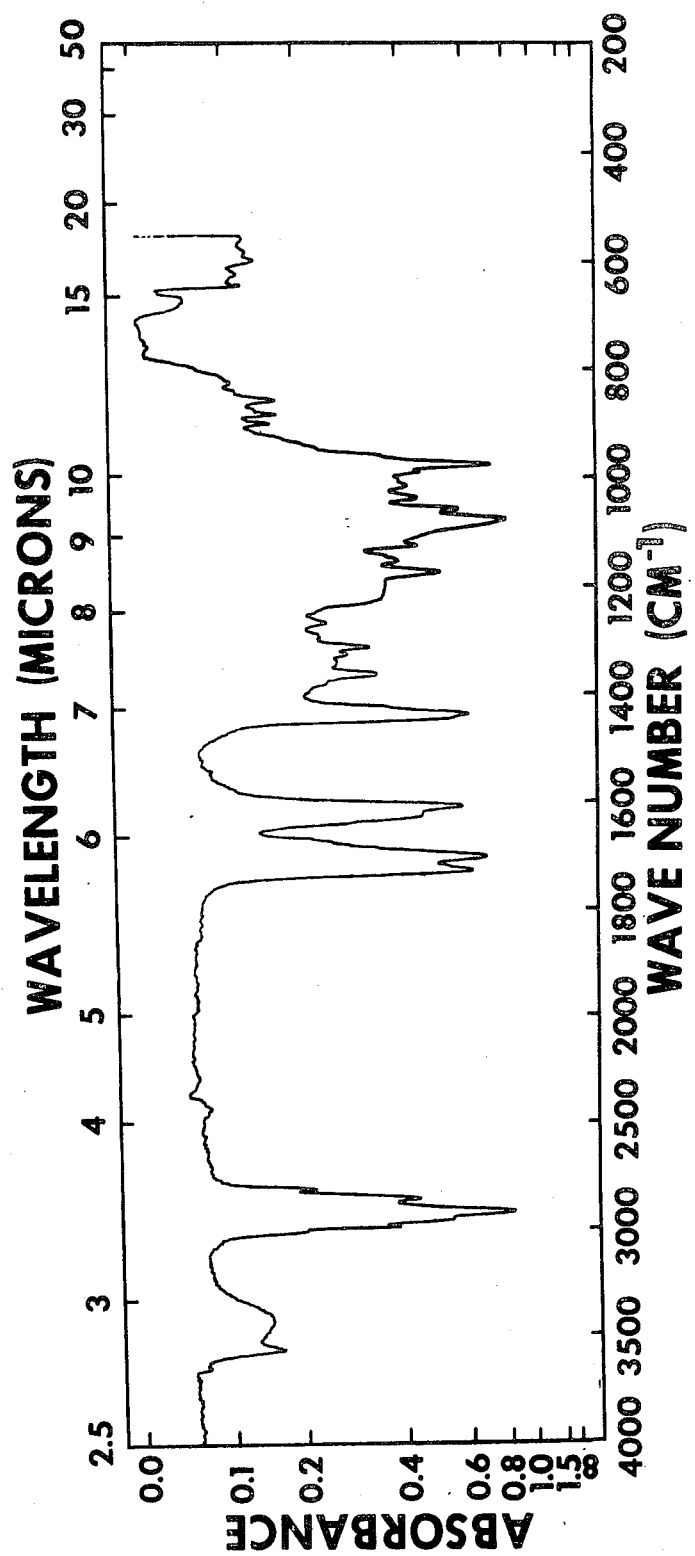

United States Patent [19]

Sehgal et al.

[11] 3,993,749
[45] Nov. 23, 1976

[54] RAPAMYCIN AND PROCESS OF PREPARATION

[75] Inventors: Surendra N. Sehgal, Dollard des Ormeaux; Teodora M. Blazekovic, Mount Royal; Claude Vezina, Deux-Montagnes, all of Canada

[73] Assignee: Ayerst McKenna and Harrison Ltd., Montreal, Canada

[22] Filed: Sept. 25, 1975

[21] Appl. No.: 616,695

Related U.S. Application Data

[60] Division of Ser. No. 460,665, April 12, 1974, Pat. No. 3,929,992, which is a continuation-in-part of Ser. No. 293,699, Sept. 29, 1972, abandoned.

[52] U.S. Cl. .............................................. 424/122

[51] Int. Cl.$^2$ .......................................... A61K 35/74
[58] Field of Search ................................... 424/122

[56] References Cited
OTHER PUBLICATIONS

Millev, The Pfizer Handbook of Microbial Metabolites, McGraw-Hill Book Co., Inc., N.Y., N.Y., 1961, p. 580.

*Primary Examiner*—Jerome D. Goldberg

[57] ABSTRACT

Antibiotic rapamycin is producible by culturing *Streptomyces hygroscopicus* NRRL 5491 in an aqueous nutrient medium. Rapamycin has antifungal properties. Methods for its preparation and use are disclosed.

2 Claims, 2 Drawing Figures

RAPAMYCIN AND PROCESS OF PREPARATION

This application is a division of application Ser. No. 460,665, filed Apr. 12, 1974, now U.S. Pat. No. 3,929,992, granted Dec. 30, 1975, which, in turn, is a continuation in part of Ser. No. 293,699, filed Sept. 29, 1972, now abandoned.

BACKGROUND OF THE INVENTION

A. Field of Invention

This invention relates to an antibiotic, a new composition of matter called rapamycin, and to a process for its preparation.

B. Description of Prior Art

The antibiotic of this invention is readily distinguished from prior art compounds of its class by its profound antifungal activity and its relatively low order of toxicity.

More explicitly, the ultra violet spectrum of rapamycin, noted herein, indicates that this compound belongs to the class of antibiotics known as triene antibiotics. In this particular class there are only five compounds reported previously, Trienine, A. Aszalos et al., J. Antibiotics, 21, 611 (1968) is a triene antibiotic with antitumor activity which also shows marked activity against gram positive organisms and only marginal activity against Candida strains. The antifungal triene reported by J. J. Armstrong, et al., Nature, 206, 399 (1965) and Mycotrienin reported by C. Coronelli et al., J. Antibiotics, 20, 329 (1967) are probably identical. Both have low antifungal activity (MIC against C. albicans: 5 $\mu$g/ml) and high toxicity ($LD_{50}$ in mice: 15 mg/kg). The remaining two antibiotics — Resistaphylin, S. Aezaiva et al., J. Antibiotics, 14, 393 (1971) and Proticin, G. Nesemann et al., Naturwissenschaften, 59, 81 (1972)- are readily distinguished from the compound of the present invention in that they exhibit antibacterial without any antifungal activity.

BRIEF SUMMARY OF THE INVENTION

Rapamycin is a chemical compound producible by culturing a rapamycin-producing organism in an aqueous nutrient medium. The compound has the property of adversely affecting the growth of fungi, for example, *Candida albicans* and *Microsporum gypseum*. Accordingly, rapamycin may be used to prevent the growth of or reduce the number of certain fungi in various environments.

The rapamycin — producing organism used for this invention, *Streptomyces hygroscopicus* NRRL 5491, was obtained from Easter Island soils and samples thereof have been deposited without restrictions with the Northern Utilization and Research Division, Agricultural Research Service, U.S. Department of Agriculture, Peoria, Illinois, U.S.A.

It is to be understood that the invention is not limited to the use of the particular organism herein described, but includes variations and mutants obtained by natural selection or by treatment of the microorganism with, for instance, ultraviolet rays, X-rays, N-methyl-N'-nitro-N-nitroso-guanidine, manganese chloride, camphor, nitrogen mustards, and the like, as well as polyploids of the varous mutants.

*Streptomyces hygroscopicus* NRRL 5491 develops abundantly in culture media usually employed for cultivation of other organisms of the same genus. It is capable of growing at temperatures ranging from 20° to 35° C., preferably at about 28° C, on Czapek's agar, glucose asparagine agar, glycerol asparagine agar, starch agar and peptone beef agar. Also, the organism grows very well on yeast extract agar, malt extract agar, starch-inorganic salts agar, oatmeal agar, oatmeal-tomato agar and Bennet's agar. On potato slices there is no aerial mycelium, but substrate growth is well developed and buff in color. On all media, the aerial growth is at first white then grayish with black spots. Sporophores are often compact, forming a spiral of more than ten spores. Substrate growth is light yellow to almost colorless and in some media pale brown. Ocasionally a yellowish pigment is produced. The organism is $H_2S$- and melanine-negative.

Carbohydrate utilization by *Streptomyces hygroscopicus* NRRL 5491 was studied in carbon utilization agar (ISP Medium 9) according to the procedure standardized by the International Streptomyces Project (ISP).

The best utilized carbohydrates were D-glucose, inositol, D-fructose and D-mannitol; less well utilized carbohydrates were rhamnose, raffinose, xylose, starch and arabinose. Carbohydrates not utilized were sucrose and cellulose.

The environment and nutritional requirements for the fermentation of *Streptomyces hygroscopicus* NRRL 5491 are similar to those necessary for the production of antibiotics by other aerobic microorganisms. Thus, aerobiosis can be sustained in a liquid nutrient medium inoculated with a sterile culture incubated in flasks placed on shaking machines. For industrial production, metal tanks with internal aeration and agitation by means of paddles can be substituted. Rapamycin is also produced by surface cultivation. The microorganism requires as nutrient elements assimilable carbon and organic nitrogenous substances. The presence of mineral salts is desirable. Cultivation is best effected when the initial pH of the culture medium is between 6.5 and 7.5, the optimum pH being aroudn 6.8-7.3.

The utilizable sources of assimilable carbon for the production of the antibiotic are very diverse, there being included sugars (for example, glucose, D-fructose, D-mannitol, maltose, arabinose, rhamnose, raffinose, xylose, and the like), dextrin, starches of different types of origina, glycerol (and other polyalcohols), inositol and animal and vegetable fats, as well as esters thereof. The sources of organic assimilable nitrogen which actively stimulate growth and favor production of rapamycin are substances such as soybean meal, cotton meal and other vegetable meals (whole or partially or totally defatted), meat flours or animal viscera, various peptones, casein hydrolysates, soybean hydrolysates, yeast hydrolysates, lactalbumin, wheat glutins, distillers solubles, corn steeps, molasses, urea and amino acids.

Mineral salts, such as the chlorides, nitrates, sulfates, carbonates and phosphates of sodium, potassium, ammonium and calcium, should be included in appropriate concentrations. The nutritive medium should contain a number of trace elements such as magnesium, iron, manganese, and zinc.

The inoculum of the above medium for the fermentation is provided with a fresh slant of *Streptomyces hygroscopicus* NRRL 5491.

Under the described conditions and with the temperature of cultivation at about 20°–35° C, preferably at about 25° C, maximum production of rapamycin in tanks is obtained in from about two to about eight days. Alternatively, the pH may be controlled during fermentation in tanks and maintained at about pH 6.0, and glucose may be added continuously from about 2 days after beginning to the end of fermentation, thus obtaining maximum yields in about four to five days.

Thereafter a variety of procedures may be employed in the isolation and purification of rapamycin, for example, solvent extraction, partition chromatography, silica gel chromatography, liquid-liquid distribution in a Craig apparatus, and crystallization from solvents. Solvent extraction procedures are preferred for commercial recovery inasmuch as they are less time consuming and less expensive.

Generally speaking, rapamycin may be harvested by one of the following methods.

a. The fermentation mixture is extracted with a substantially water-immiscible solvent, preferably a lower alkanol, for example n-butanol, n-pentanol or the commercial mixture of pentanols known as "Pentasol" or n-hexanol, or a substantially water-immiscible lower alkyl lower alkanoate, for example, ethyl acetate, buryl acetate, amyl acetate or the commercially available mixture of amyl acetates, or a substantially water-immiscible halogenated aliphatic hydrocarbon, for example, chloroform, methylene dichloride or dichloroethane. The extracts are dried and concentrated under reduced pressure to yield an oily residue which is in turn extracted with a water-miscible solvent, preferably a lower alkanol, for example methanol or ethanol. Said last-named extracts are filtered through diatomaceous earth ("Celite"), and the filtrate concentrated under reduced pressure to yield an oily residue containing crude rapamycin.

b. The fermentation mixture is filtered through a pad of diatomaceous earth ("Celite") and the filter cake containing the mycelium is extracted as described below under (c). The filtrate, i.e. the mycelium-free fermentation mixture, is extracted several times with a substantially water-immiscible solvent, for example, a lower alkanol, lower alkyl lower alkanoate or halogenated aliphatic hydrocarbon as exemplified above in section (a). The extracts are dried and concentrated under reduced pressure to yield an oily residue which is extracted with a water-miscible solvent, preferably a lower alkanol, for example methanol or ethanol. Said last-named extracts are treated in the same manner as described above under (a) to yield an oily residue containing crude rapamycin.

c. The mycelium is separated from the fermentation mixture and extracted with a suitable water-miscible solvent, preferably a lower alkanol, for example methanol or ethanol. The extract is concentrated by evaporation to the aqueous phase, which in turn is extracted with a substantially water-immiscible solvent, such as a lower alkyl lower alkanoate, halogenated aliphatic hydrocarbon or a substantially water-immiscible lower alkanol as described above or an aromatic hydrocarbon, for example benzene or toluene. The latter extract is evaporated under reduced pressure to yield an oily residue containing crude rapamycin.

The crude rapamycin obtained by any of the processes described in sections (a), (b), or (c) is then purified by a variety of methods, for example, see above. Preferred methods include absorption of the crude rapamycin on an absorbent, for instance charcoal or silica gel from a solution in a substantially nonpolar, first solvent, followed by elution therefrom with a second solvent, more polar than said first solvent.

DETAILS OF THE INVENTION

Rapamycin is useful as an antifungal agent against a number of pathogenic fungi; for example, *Candida albicans*, and other candida species, *Microsporum gypseum*, *Trichophyton mentagrophytes*, *Asperqillus sp.*, and *Sporotrichum sp.*.

The inhibitory activity of rapamycin is especially pronounced against *Candida albicans* and said last organism may be used advantageously for assay purposes.

The antifungal activity of this compound is demonstrable in standard tests used for this purpose, for example, in the tests described in "Antiseptics, Disinfectants, Fungicides and Sterilization", G. F. Reddish, Ed., 2nd ed., Lea and Febiger, Philadelphia, 1957 or by D. C. Grove and W. A. Randall in "Assay Methods of Antibiotics", Med. Encycl. Inc., New York 1955.

When the antibiotic of this invention is employed as an antifungal agent in warm-blooded animals, e.g. rats, it may be used alone or in combination with pharmaceutically acceptable carriers, the proportion of which is determined by the solubility and chemical nature of the compound, chosen route of administration and standard biological practice. For example, an antifungally effective amount of the antibiotic may be administered orally in solid form containing such excipients as starch, sugar, certain types of clay and so forth. Similarly, such an amount may also be administered orally in the form of solutions or suspensions, or the antibiotic may be injected parenterally. For parenteral administration the antibiotic may be used in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The dosage of the present antibiotic will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound of this invention is most desirably administered at a concentration level that will generally afford antifungally effective results without causing any harmful or deleterious side effects and preferably at a level that is in a range of from about 1.0 mg to about 250 mg per kilo per day, although as aforementioned variations will occur. However, a dosage level that is in the range of from about 10 mg to about 100 mg per kilo per day is most desirably employed in order to achieve effective results.

In addition, the agent may be employed topically. For topical application it may be formulated in the form of solutions, creams, or lotions in pharmaceutically acceptable vehicles containing 0.1 – 5 percent, preferably 2 percent of the agent, and may be administered topically to the infected area of the skin.

Rapamycin may also be used for cleaning and disinfecting laboratory equipment, surgical instruments, locker rooms, or shower rooms of sensitive fungus organisms. For such purposes it is preferred to use 0.1 – 10% solutions of rapamycin in a lower alkanol, preferably methanol, diluted with 10 – 100 volumes of water containing 0.001 – 0.1% of a non-ionic surfaceactive agent, for example, polysorbate 80 U. S. P., immediately before applying it to the objects to be cleaned and disinfected.

PREPARATION

In one embodiment of this invention rapamycin is prepared in the following manner:

A suitable fermenter is charged with production medium 8KM (see Example 1). After sterilization and cooling, the medium is inoculated with a first stage inoculum preparation of *Streptomyces hygroscopicus* NRRL 5491.

A maximum titre of 20 to 100 µg/ml of the antibiotic is reached in the fermentation mixture after 2–8 days, usually after about 5 days, as determined by the cup plate method and *Candida albicans* as the test organism. The mycelium is harvested by filtration with diatomaceous earth. Rapamycin is then extracted from the mycelium with a water-miscible solvent, for example a lower alkanol, preferably methanol or ethanol. The latter extract is then concentrated, preferably under reduced pressure, and the resulting aqueous phase is extracted with a water-immiscible solvent. A preferred water-immiscible solvent for this purpose is methylene dichloride although chloroform, carbon tetrachloride, benzene, n-butanol and the like may also be used. The latter extract is concentrated, preferably under reduced pressure, to afford the crude product as an oil.

The product may be purified further by a variety of methods. Among the preferred methods of purification is to dissolve the crude product in a substantially non-polar, first solvent, for example petroleum ether or hexane, and to treat the resulting solution with a suitable absorbent, for example charcoal or silica gel, so that the antibiotic becomes absorbed on the absorbant. The absorbant is then separated and washed or eluted with a second solvent more polar than the first solvent, for example ethyl acetate, methylene dichloride, or a mixture of methylene dichloride and ether (preferred). Thereafter, concentration of the wash solution or eluate affords substantially pure rapamycin. Further purification is obtained by partial precipitation with a non-polar solvent, for example, petroleum ether, hexane, pentane and the like, from a solution of the rapamycin in a more polar solvent, for example, ether, ethyl acetate, benzene and the like. Still further purification is obtained by column chromatography, preferably employing silica gel, and by crystallization of the rapamycin from ether.

In another preferred embodiment of this invention a first stage inoculum of *Streptomyces hygroscopicus* NRRL 5491 is prepared in small batches in a medium containing soybean flour, glucose, ammonium sulfate, and calcium carbonate incubated at about 25° C at pH 7.1 – 7.3 for 24 hrs. with agitation, preferably on a gyrotary shaker. The growth thus obtained is used to inoculate a number of somewhat larger batches of the same medium as described above which are incubated at about 25° C and pH 7.1 – 7.3 for 18 hrs. with agitation, preferably on a reciprocating shaker, to obtain a second stage inoculum which is used to inoculate the production stage fermenters.

The production stage fermenters are equipped with devices for controlling and maintaining pH at a predetermined level and for continuous metered addition of nutrient. They are charged with a medium containing soybean flour, glucose, ammonium sulfate, and potassium phosphate, sterilized, and the pH is adjusted to pH 5.8 – 6.2. The fermenters are inoculated with the second stage inoculum described above and incubated at about 25° C with agitation and aeration while controlling and maintaining the mixture at approximately pH 6.0 by addition of a base, for example, sodium hydroxide, potassium hydroxide or preferably ammonium hydroxide, as required from time to time. Addition of a source of assimilable carbon, preferably glucose, is started when the concentration of the latter in the broth has dropped to about 0.5% wt/vol, normally about 48 hrs after the start of fermentation, and is maintained until the end of the particular run. In this manner a fermentation broth containing about 60 µg/ml of rapamycin as determined by the assay method described above is obtained in 4 — 5 days, when fermentation is stopped.

Filtration of the mycelium, mixing the latter with a water-miscible lower alkanol, preferably methanol, followed by extraction with a halogenated aliphatic hydrocarbon, preferably trichloroethane, and evaporation of the solvents yields a first oily residue. This first oily residue is dissolved in a lower aliphatic ketone, preferably acetone, filtered from insoluble impurities, the filtrate evaporated to yield a second oily residue which is extracted with a water-miscible lower alkanol, preferably methanol, and the latter extract is evaporated to yield crude rapamycin as a third oily residue. This third oily residue is dissolved in a mixture of a lower aliphatic ketone and a lower aliphatic hydrocarbon, preferably acetone-hexane, an absorbent such as charcoal or preferably silica gel is added to adsorb the rapamycin, the latter is eluted from the adsorbate with a similar but more polar solvent mixture, for example a mixture as above but containing a higher proportion of the aliphatic ketone, the eluates are evaporated and the residue is crystallized from diethyl ether, to yield pure crystalline rapamycin. In this manner a total of 45–58% of the rapamycin initially present in the fermentation mixture is recovered as pure crystalline rapamycin.

CHARACTERIZATION a. Purified rapamycin is a colourless crystalline compound, m.p. 183°–185° C after recrystallization from ether;

b. rapamycin is soluble in ether, chloroform, acetone, methanol and dimethylformamide; very sparingly soluble in hexane and petroleum ether and substantially insoluble in water;

c. rapamycin shows a uniform spot on thin layer plates of silica gel G (E. Merck A. G., Darmstadt) developed with a variety of thin layer chromatography solvent systems; for example, ether-hexane 40:60 (Rf = 0.42), isopropyl alcohol-benzene 15:85 (Rf = 0.5) and ethanol-benzene 20:80 (Rf = 0.43);

d. rapamycin obtained from four successive fermentation batches gave the following values on repeated elemental analyses:

|    |        |        |        |       | AVERAGE |
|----|--------|--------|--------|-------|---------|
| C% | 67.24, | 66.14, | 67.26, | 66.72.| 66.84   |
| H% | 8.93,  | 8.72,  | 8.92,  | 8.9.  | 8.84    |
| N% | 1.39,  | 1.37,  | 1.28,  | 1.38. | 1.37    | e. rapamycin exhibits the following characteristic absorption maxima in its ultraviolet absorption spectrum (95% ethanol):

267 nm ($E_{1cm}^{1\%}$ 417), 277 nm ($E_{1cm}^{1\%}$ 541) and 288 nm ($E_{1cm}^{1\%}$ 416);

f. the infrared absorption spectrum of rapamycin in chloroform is reproduced in FIG. 1 and shows characteristic absorption bands at 3560, 3430, 1730, 1705 and 1630-1610 cm$^{-1}$;

Further infrared absorption bands are characterized by the following data given in reciprocal centimeters with (s) denoting a strong, (m) denoting a medium, and (w) denoting a weak intensity band. This classification is arbitrarily selected in such a manner that a band is denoted as strong (s) if its peak absorption is more than 2/3 of the background in the same region; medium (m) if its peak is between 1/3 and 2/3 of the background in the same region; and weak (w) if its peak is less than ⅓ of the background in the same region.

Figure 2:
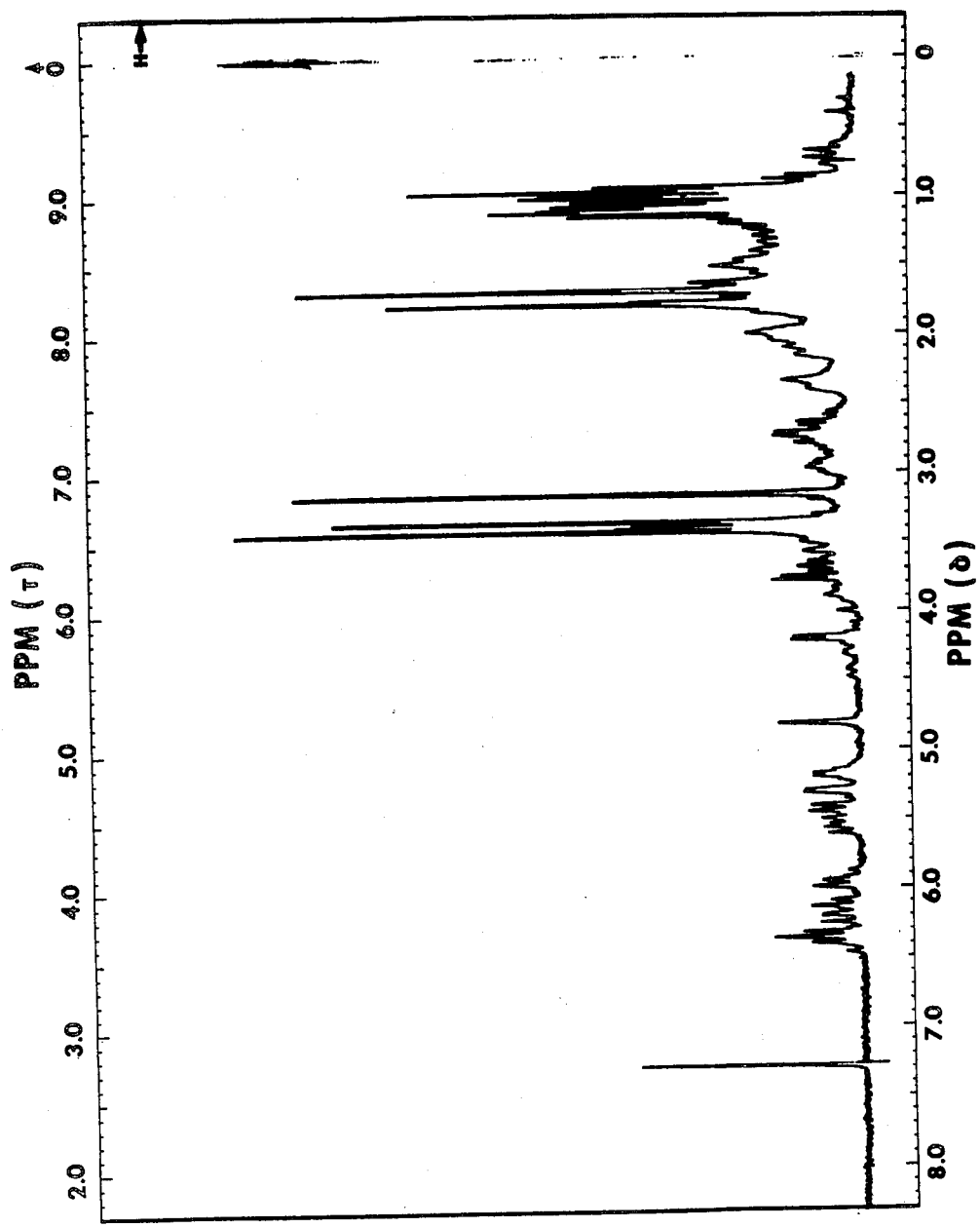

| | |
|---|---|
| 2990 cm$^{-1}$ (m) | 1158 cm$^{-1}$ (m) |
| 2955 cm$^{-1}$ (s) | 1129 cm$^{-1}$ (s) |
| 2919 cm$^{-1}$ (s) | 1080 cm$^{-1}$ (s) |
| 2858 cm$^{-1}$ (s) | 1060 cm$^{-1}$ (s) |
| 2815 cm$^{-1}$ (m) | 1040 cm$^{-1}$ (m) |
| 1440 cm$^{-1}$ (s) | 1020 cm$^{-1}$ (m) |
| 1365 cm$^{-1}$ (m) | 978 cm$^{-1}$ (s) |
| 1316 cm$^{-1}$ (m) | 905 cm$^{-1}$ (m) |
| 1272 cm$^{-1}$ (m) | 888 cm$^{-1}$ (w) |
| 1178 cm$^{-1}$ (s) | 866 cm$^{-1}$ (w) | g. the nuclear magnetic resonance spectrum of rapamycin in deuterochloroform is reproduced in FIG. 2;

h. the minimum inhibitory concentration of rapamycin against various microorganism is listed below:

| Organisms | Rapamycin: ($\mu$g/ml) |
|---|---|
| Candida albicans (5 strains) | 0.02 to 0.1 |
| C. catenulata | < 0.1 |
| C. lipolytica | 2.5 |
| C. stellatoidea | < 0.1 |
| C. tropicalis | 0.1 |
| C. pseudtropicalis | > 5.0 |
| C. parapsilosis | < 0.1 |
| C. morrera | < 0.1 |
| C. intermedia | < 0.1 |
| M. gypseum | 12.5 |
| T. mentagrophytes | > 1000 | i. rapamycin exhibits a LD$_{50}$ (i.p., mice) of 597.3 ± 28.1 mg/kg and a LD$_{50}$ (p.o., mice) of >2,500 mg/kg.

In protection studies, mice were infected by intravenous injection of C. albicans ATCC 11651. At 1, 4 and 24 hours after infection, mice were administered 10 mg/kg (s. c.) of rapamycin. At this dose 50% of the mice were protected. Treatment with 25 mg/kg (s.c.) offered complete protection. When rapamycin was administered orally, at 10 mg/kg 4 out of 10 mice survived, and at 25 mg/kg complete protection was observed.

A 1% suspension (0.2 ml) of rapamycin in water containing 1.5% polysorbate 80 (Tween 80), when injected intradermally into a rabbit's ear caused no irritation. Similarly, two drops of a 0.5% suspension applied to a rabbit's eye caused no irritation.

The following Examples illustrate further this invention.

EXAMPLE 1

Microorganism

Streptomyces hygroscopicus NRRL 5491 was grown and maintained on oatmeal-tomato paste agar slants (T. G. Pridham, et al., Antibiotic Annual 1956–1957, Medical Encyclopedia Inc., New York, p. 947) and in Roux bottles containing the same medium. Good growth was obtained after 7 days of incubation at 28° C. Spores from one Roux bottle were washed off and suspended into 50 ml of sterile distilled water. This suspension was used to inoculate the first stage inoculum.

The first-stage inoculum medium consisted of Emerson broth [R. L. Emerson et al., J. Bacteriol, 52, 357 (1946)] 0.4%; peptone, 0.4%; sodium chloride, 0.25%; yeast extract, 01.%; and glucose, 1%; pH 7.0; flasks containing the above medium were inoculated with 1% of the spore suspension described above. The inoculated flasks were incubated for 30 hrs. at 28°C on a reciprocating shaker set at 65 r.p.m. (4 inch stroke).

Production stage

The production stage was run in 250-liter New Brunswick fermenters Model F-250, equipped with automatic antifoam addition system and pH recorder-controller. The fermenters were charged with 160 liters of an aqueous production medium (8 KM) consisting of the following constituents:

| | |
|---|---|
| soluble starch | 1.0% |
| (NH$_4$)$_2$SO$_4$ | 0.5% |
| K$_2$HPO$_4$ | 0.5% |
| glucose (Cerelose) | 1.5% |
| MgSO$_4$ | 0.025% |
| ZnSO$_4$ | 0.005% |
| MnSO$_4$ | 0.001% |
| FeSO$_4$ . 7H$_2$O | 0.002% |
| CaCO$_3$ | 0.2% |
| "Blackstrap" molasses | 0.5% |
| hydrolyzed casein (NZ-Case, Sheffield Chemical, Norwich, New York) | 0.5% |
| lard oil (Larex No. 1, Swift Canadian Co., Toronto) | 0.2% |
| pH 7.1 to 7.3 | |

The fermenters were sterilized at 121° C for 45 minutes, cooled and inoculated with one flask (2% inoculum) of first stage inoculum. Incubation temperature: 28° C; aeration: 0.5 vol/vol/min.; agitation: 250 r. p. m.

A titre of ca. 20 $\mu$g/ml, determined by microbiological assay on agar plates seeded with Candida albicans, was reached in 5 days. The fermentation was stopped.

Extraction and isolation of the antibiotic was performed by one of the following methods:

EXTRACTION a. The fermentation mixture was extracted twice with 1 v/v of n-butanol. The combined butanol extracts were washed with 1 v/v of water, dried with anhydrous sodium sulfate and evaporated to dryness under reduced pressure to yield a residue. The oily residue was extracted three times with 2 litres of methanol. The combined methanol extracts were passed through diatomaceous earth ("Celite") and evaporated to dryness to yield an oily residue containing crude rapamycin.

b. The fermentation mixture was filtered over diatomaceous earth ("Celite"). The filtrate was extracted twice with 1 v/v of ethyl acetate. The ethyl acetate extracts were washed with 1 volume of water, dried with anhydrous sodium sulfate and evaporated under reduced pressure to dryness. The residue was extracted twice with 1 liter of methanol. The methanol extracts were evaporated under reduced pressure to yield an oily residue containing crude rapamycin.

c. The mycelium obtained as described under section (b) was washed with 1 to 2 volumes of water. The washed mycelium was extracted three times with 5 volumes of methanol per weight of wet mycelium each time. The methanolic extracts were pooled and concentrated under reduced pressure to a small volume of an aqueous phase containing approximately 10% v/v of methanol. This aqueous phase was extracted three times with 1 vol. of methylene chloride; the methylene chloride extracts were combined, dried with anhydrous sodium sulfate and evaporated to yield an oily residue.

The oily residue was diluted with 1 volume of petroleum ether, and 30% w/v of charcoal (Darco G60) was added. The mixture was stirred for half an hour and filtered. The charcoal, which retained substantially all of the product, was washed twice with one volume of petroleum ether. The charcoal was eluted three times with 5 vol. (based on the weight of the charcoal) of a mixture of methylene chloride and ether (50:50). The methylene chloride-ether extracts were evaporated to dryness and the residue dissolved in a small amount of ether. The crude product was obtained by precipitation from the ether solution with cold petroleum ether.

Alternatively, the oily residue obtained by any of the extraction procedures described above was diluted with 1 vol. of hexane and passed through a preparative column of silica gel G. The product was absorbed on the column. The silica gel G containing absorbed product was washed with several volumes of hexane and 50:50 hexane-ether mixtures. The product was eluted from the column with ether. The ether eluant was evaporated to a small volume and crude product obtained by precipitation from the ether solution with cold petroleum ether.

Purification

The aforementioned crude product was purified further by column chromatography on silica gel G Merck (50:1 w/v) in hexane-ether (50:50). The product was eluted from the column with ether. The ether eluate was evaporated to a small volume. Purified rapamycin was precipitated with petroleum ether. The analytical samples were prepared by crystallization from ether, m.p. 183°–185° C.

EXAMPLE 2

*Streptomyces hygroscopicus* NRRL 5491 is grown and spores are obtained in the same manner as described in Example 1.

First Stage Inoculum

Erlenmeyer flasks (500 ml) are filled with 100 ml of the following medium:

| | | |
|---|---|---|
| Soybean flour (Archer-Daniels Co., Midland, Mich. "Special X") | = 4% | wt/vol |
| Glucose (Cerelose) | = 2% | wt/vol |
| Ammonium sulfate | = 0.3% | wt/vol |
| Calcium carbonate | = 0.15% | wt/vol |
| Water to volume, pH 7.1 to 7.3 | | |

The flasks are sterilized at 121° for 35 minutes and cooled to 25°. The flasks are inoculated with 4% (4 ml) of spore suspension described above and incubated on a gyrotary shaker (2 inch stroke) at 240 rpm for 24 hrs at 25° C.

Second Stage Inoculum

Twenty-four liter flat bottom flasks containing 3.2 l of the inoculum medium described above at pH 7.1 – 7.3 are sterilized by autoclaving at 121° for 35 minutes, shaken to resuspend the insoluble material and resterilized for another 45 minutes. The flasks are cooled to 25° and inoculated with 64 ml of first stage inoculum, placed on a reciprocating shaker (4 inches stroke) set at 65 rpm and incubated for 18 hrs at 25° C.

Production Stage

The production stage is run in 250 liter New Brunswick fermenters Model F-250 equipped with automatic antifoam addition system and pH recorder-controller. The fermenters are charged with 160 liters of an aqueous production medium consisting of the following constituents:

| | | |
|---|---|---|
| Soybean flour (Archer-Daniels Co., Midland, Mich., "Special X") | = 3% | wt/vol |
| Glucose (Cerelose) | = 2% | wt/vol |
| Ammonium sulfate | = 0.1% | wt/vol |
| Potassium phosphate (monobasic) | = 0.5% | wt/vol |
| Antifoaming Agent ("DF-143 - PX" Mazer Chemicals, Inc., Gurnee, Ill.,) | = 0.05% | wt/vol |

The fermenters are sterilized at 121° C for 30 minutes, cooled, and the pH is adjusted to 5.8 to 6.2 with ammonium hydroxide. They are then inoculated with one flask (2%) of second stage inoculum and fermentation is allowed to proceed at 25° C, with aeration at 0.25 v/v/min and agitation at 200 rpm.

The pH of the fermentation broth starts to drop at 30 – 35 hours and is controlled at 6.0 until the end of fermentation by the automatic, on demand, addition of ammonium hydroxide. At about 48 hrs. of propagation the glucose concentration in the broth drops to about 0.5%, and continous addition of 40% glucose solution is started at a rate of 3.75% of fermentation mixture volume per day and continued until the end of fermentation. A titer of about 60 μg/ml. determined by microbiological assay on agar plates seeded with Candida albicans is reached in 4 to 5 days. The fermentation is stopped at this point.

Extraction and isolation of the antibiotic is performed by the following procedure:

The fermentation mixture is filtered over diatomaceous earth (Celite) to recover the mycelium. A typical 400 liter batch obtained from three fermenters yields about 60 kg of wet mycelium. The wet mycelium is mixed with 1 vol/wt of methanol by agitation and the mixture is extracted twice with 2 vol of trichloroethane (methyl chloroform), yielding about 250 liters of trichloroethane extract containing about 22 – 24 g of rapamcyin. The trichloroethane extract is evaporated to dryness under reduced pressure to yield 1 to 1.4 kg of oily residue. This residue is added slowly with agitation to 5 vols of acetone and the resulting precipitate is separated by filtration. The acetone solution is evaporated to dryness under reduced pressure to yield an oily residue. This oily residue is extracted twoce with 2 and 1 vols of methanol respectively. The combined methanol extracts are filtered and the remaining oil is discarded. The methanol extract containing rapamycin is evaporated to dryness under reduced pressure to yield 200 to 300 g of oily residue. This residue is dissolved in 5 v/wt of 15% acetone in hexane. To this solution of the oily residue, silica gel (Merck) is added in an amount equal to twice the weight of the oily residue and the mixture is stirred for about one hr. The mixture is filtered on a sintered glass funnel and the filitrate rejected. The silica gel containing rapamycin is washed with several volumes of 15% acetone in hexane. The washed silica gel is eluted with 30% acetone in hexane. The eluant is evaportated to dryness to yield about 60 to 150 g of dry residue. The dry residue is dissolved in ether and pure rapamycin is separated by crystallization. A typical run containing about 24 g of crude rapamycin yields between 10 and 14 g of pure crystalline product.

We claim:

1. A pharmaceutical composition which comprises a pharmaceutically acceptable carrier and an antifungally effective amount of the antibiotic rapamycin which
    a. is a colourless, crystalline compound with a melting point of 183° to 185° C, after recrystallization from ether;
    b. is soluble in ether, chloroform, acetone, methanol and dimethylformamide, very sparingly soluble in hexane and petroleum ether and substantially insoluble in water;
    c. shows a uniform spot on thin layer plates of silica gel;
    d. has a characteristic elemental analysis of about C, 66.84%; H, 8.84% N, 1.37%;
    e. exhibits the following characteristic absorption maxima in its ultraviolet absorption spectrum (95% ethanol): 267 nm ($E_{1cm}^{1\%}$ 417), 277 nm ($E_{1cm}^{1\%}$ 541) and 288 nm ($E_{1cm}^{1\%}$ 416);
    f. has a characteristic infrared absorption spectrum shown in accompanying FIG. 1;
    g. has a characteristic nuclear magnetic resonance spectrum as shown in accompanying FIG. 2;
    h. has a minimum inhibitory concentration of 0.02 to 0.1 μg/ml against *Candida albacans;* and
    i. exhibits a $LD_{50}$ (i.p., mice) of 597.3 ± 28.1 mg/kg and a $LD_{50}$ (p.o., mice) of >2,500 mg/kg.

2. A method of inhibiting the growth of pathogenic fungi in a mammal which comprises administering to said mammal an antifungally effective amount of the antibiotic rapamycin which
    a. is a colourless, crystalline compound with a melting point of 183° to 185° C, after recrystallization from ether;
    b. is soluble in ether, chloroform, acetone, methanol and dimethylformamide, very sparingly soluble in hexane and petroleum ether and substantially insoluble in water;
    c. shows a uniform spot on thin layer plates of silica gel;
    d. has a characteristic elemental analysis of about C, 66.84%; H, 8.84%; N, 1.37%;
    e. exhibits the following characteristic absorption maxima in its ultraviolet absorption spectrum (95% ethanol); 267 nm ($E_{1cm}^{1\%}$ 417), 277 nm ($E_{1cm}^{1\%}$ 541) and 288 nm ($E_{1cm}^{1\%}$ 416);
    f. has a characteristic infrared absorption spectrum shown in accompanying FIG. 1;
    g. has a characteristic nuclear magnetic resonance spectrum as shown in accompanying FIG. 2;
    h. has a minimum inhibitory concentration of 0.02 to 0.1 μg/ml against *Candida albicans;* and
    i. exhibits a $LD_{50}$ (i.p., mice) of 597.3 ± 28.1 mg/kg and a $LD_{50}$ (p.o., mice) of >2,500 mg/kg.

* * * * *